US009522047B2

United States Patent
Seibold et al.

(10) Patent No.: US 9,522,047 B2
(45) Date of Patent: Dec. 20, 2016

(54) SURGICAL MANIPULATION INSTRUMENT

(75) Inventors: Ulrich Seibold, Burnaby (CA); Sophie Thielmann, Munich (DE); Michael Strohmayr, Munich (DE)

(73) Assignee: DEUTSCHES ZENTRUM FUER LUFT-UND RAUMFAHRT E.V., Cologne (DE)

( * ) Notice: Subject to any disclaimer, the term of this patent is extended or adjusted under 35 U.S.C. 154(b) by 403 days.

(21) Appl. No.: 13/514,225

(22) PCT Filed: Nov. 30, 2010

(86) PCT No.: PCT/EP2010/068505
§ 371 (c)(1),
(2), (4) Date: Aug. 1, 2012

(87) PCT Pub. No.: WO2011/069862
PCT Pub. Date: Jun. 16, 2011

(65) Prior Publication Data
US 2012/0296341 A1    Nov. 22, 2012

(30) Foreign Application Priority Data

Dec. 7, 2009 (DE) .......................... 10 2009 056 982

(51) Int. Cl.
*A61B 34/00* (2016.01)
*A61B 17/00* (2006.01)

(52) U.S. Cl.
CPC ................ *A61B 34/70* (2016.02); *A61B 34/71* (2016.02); *A61B 2017/00477* (2013.01); *A61B 2090/0813* (2016.02)

(58) Field of Classification Search
CPC ............ A61B 17/29; A61B 2017/2929; A61B 17/1608; A61B 34/30; A61B 17/00234; A61B 34/71; A61B 37/37; A61B 34/70; A61B 2034/715
(Continued)

(56) References Cited

U.S. PATENT DOCUMENTS 6,197,017 B1   3/2001   Brock et al.
6,491,707 B2  12/2002   Makower et al.
(Continued)

FOREIGN PATENT DOCUMENTS

EP    0598202        5/1994
WO    2009102102     8/2009

OTHER PUBLICATIONS

International Preliminary Report on Patentability in corresponding International Application No. PCT/EP2010/068505, dated Jun. 7, 2012.
(Continued)

*Primary Examiner* — Katherine M Shi
*Assistant Examiner* — Michael Mendoza
(74) *Attorney, Agent, or Firm* — Ohlandt, Greeley, Ruggiero & Perle, LLP

(57) ABSTRACT

A surgical manipulation instrument which is particularly suitable for minimal invasive surgery, comprising an extra-corporeal drive device to which several axially displaceable first actuation elements are connected. The disclosure also relates to a partial intra-corporeal manipulator part which comprises several axially displaceable second actuation devices for actuating an end effector. Pairs of actuation elements are detachably connected together by means of a coupling device. A pivotable intermediate element is provided between the second coupling element and the second actuation element.

18 Claims, 6 Drawing Sheets

(58) Field of Classification Search
USPC .......................................................... 606/205
See application file for complete search history.

(56) References Cited

U.S. PATENT DOCUMENTS

| | | |
|---|---|---|
| 2001/0031983 A1 | 10/2001 | Brock et al. |
| 2003/0036748 A1 | 2/2003 | Cooper et al. |
| 2008/0046122 A1* | 2/2008 | Manzo et al. ................ 700/245 |
| 2008/0177283 A1 | 7/2008 | Lee et al. |
| 2008/0249551 A1 | 10/2008 | Sunaoshi et al. |

OTHER PUBLICATIONS

Written Opinion of the International Search Authority in corresponding International Application No. PCT/EP2010/068505, dated Jun. 7, 2012.
International Search Report dated Apr. 19, 2011 for PCT application No. PCT/EP2010/068505.

* cited by examiner

SURGICAL MANIPULATION INSTRUMENT

BACKGROUND

1. Field of the Disclosure

The disclosure refers to a surgical manipulation instrument comprising a coupling detachably connecting an extra-corporeal drive portion and a partially intra-corporeal manipulator part.

2. Discussion of the Background Art

Surgical instruments that are not designed for single use, but for multiple use, have to be sterilized after each single use. Sterilizing can be performed using non-thermal or thermal methods. In everyday clinical practice, sterilizing is generally performed using thermal methods, in particular the so-called autoclaving. In autoclaving, the instrument to be sterilized is exposed for a certain time to water vapor under very high pressure which must wet all surfaces to be sterilized. In the autoclave, the instrument to be sterilized is exposed to temperatures up to 156° C. and pressures up to 2 bar for a period of up to 40 min. Autoclaving must be repeated after each use of the instrument so that in the course of an instrument's lifetime up to several hundreds of autoclaving processes may be passed.

Ever since the 1980ies, the importance of so-called minimally invasive surgery has increased. Here, long, slender manipulation instruments are advanced through only small openings in the epidermis. The intra-corporeal operative field is observed using a rod-shaped camera, introduced in the same manner, and an extra-corporeal monitor. Minimally invasive surgery offers advantages in particular for the patient, namely little traumatizing, short convalescence times, less post-operative pain, lower blood loss, lower risk of infection, lower risk of wound healing disturbances, better cosmetic results, etc. The disadvantages of minimally invasive surgery include, among others, the limited freedom of movement of the surgical instruments. Since the passage opening in the epidermis and the fat tissue can be seen as being a stationary opening forming an invariable point, this results in inverted movement ratios or an impeded hand-eye coordination with respect to the monitor image. Two degrees of freedom of movement are bound by the invariable point, i.e. not every point in the working area can be reached under any optional orientation of the functional instrument end.

Minimally invasive manipulation instruments that offer additional intra-corporeal degrees of freedom of movement may provide enhanced intra-corporeal manipulability and thus represent a considerable improvement in minimally invasive surgery. The additional degrees of freedom have to be moved precisely. This may possibly be achieved by manual operation, however, this requires great aptness and long practice. Therefore, a robot-assisted remote manipulation approach is advisable, where the surgeon sits at an ergonomically shaped console, remote from the patient, and guides the surgical manipulation instrument via an appropriate man-machine interface without having to think about the cinematic and its activation. Here, the surgical manipulation instrument is actuated in a computer-assisted manner and performs the movement corresponding to the surgeon's intentions.

However, the actuators for driving the surgical manipulation instrument can generally not be autoclaved. Therefore, it is required that the extra-corporeal drive portion is separable from the partially intra-corporeal manipulator part.

The surgical manipulation instrument is thus bipartite and, by means of a coupling, is adapted to be separated into an extra-corporeal drive portion and an intra-corporeal manipulator part.

A surgical manipulation instrument is known from U.S. Pat. No. 6,491,707 A1, which comprises a coupling for separating the drive portion from the manipulator part. Here, the drive device rotates actuation elements such as shafts and transmits the rotational and torsional movements to actuation elements of the manipulator part via the coupling device. The end effector of the manipulator part is actuated through the second actuation elements. The coupling parts each have rotatable coupling bodies comprising axial pins and bores, respectively, and are coupled or uncoupled in the axial direction. Since the rotatable opposite coupling bodies cannot be coupled together if they are not in precise alignment, a search run must be performed for all coupling body pairs upon coupling. The coupling bodies each rotate until a position is found in which all coupling body pairs are in a coupling position that allows engagement. A similar coupling is known from US 2001 003 1983 A1. Here, the coupling pats comprise semi-cylindrically shaped coupling bodies. In the interest of a smooth coupling operation it is necessary to provide a certain minimum play between the coupling bodies in the engaged condition. However, this play has adverse effects in the operation of the manipulation instrument or may even make an automatic control impossible.

It is an object of the disclosure to provide a surgical manipulation instrument comprising axially displaceable elements both on the drive side and on the manipulator side, wherein the actuation elements are connected by means of a reliable and simple coupling device.

SUMMARY

Newly developed drive means generating axial movements allow an axial displacement, i.e. a displacement in the longitudinal direction, of first actuation elements, such as cables or rods, connected with the drive means, instead of rotating the same. It is also desirable to provide axially displaceable second actuation elements also on the part of the manipulator part in order to actuate the end effector. A linear actuation of the end effector is advantageous with a view to manipulability.

The surgical manipulation instrument of the present disclosure, which is particularly suited for minimally invasive surgery, comprises an extra-corporeal drive portion as well as a manipulator part adapted for partial intra-corporeal arrangement. The drive means has a plurality of axially displaceable first actuation elements. The actuation elements may be rods or cables, for instance, via which axial forces are transmitted. The manipulator part also comprises a plurality of axially displaceable, second actuation elements which are also rods and/or cables, for instance. The actuation elements serve to actuate an end effector.

The first actuation elements are connected with the second actuation elements via a coupling device. The coupling device provides for a detachable connection of actuation element pairs. The coupling device comprises a first coupling element connected with the first actuation element. Further, the coupling device comprises a second coupling element that is connected with the second actuation element. Preferably, at least two actuation elements are provided which are connected through corresponding coupling devices so that a first and a second actuation element form a respective actuation element pair. According to the disclosure, a pivotable intermediate element is provided between the second coupling element and the second actuation element. Of course, a corresponding pivotable intermediate element may also be provided between the first coupling element and the first actuation element, the disclosure being hereinafter described with reference to a pivotable intermediate element provided between the second coupling element and the second actuation element. The pivotable intermediate element serves to translate an axial movement of the first actuation element into a pivot movement. The pivot movement of the intermediate element then causes an axial movement of the second actuation element. Depending on the design of the pivotable intermediate element it is possible, for instance, to realize an increase or decrease in the movement of the first actuation element. In particular, it is possible to decrease the movement of the first actuation element such that the second actuation element travels a shorter distance. This allows for a very precise handling.

In a preferred development of the disclosure the second coupling element comprises a pivot arm. Preferably, the pivot arm is integrally connected with the intermediate element. In this embodiment it is preferred that the pivot arm is connected with the first coupling element, the connection in particular being a rigid connection. By axially displacing the first actuation element, the pivot arm is pivoted about the axis of the pivotable intermediate element.

In order to connect the pivot arm with the first coupling element, the pivot arm preferably comprises a bifurcated recess. A projection of the first coupling element engages this bifurcated recess. Here, the recess may have a circular cylindrical cross section, for example. The bifurcated recess is slot-shaped and has a rounded end portion so that the surface contact between the projection and the recess is as large as possible in this region. The recess and the projection are preferably adapted with respect to their outer shape so as to realize as large a surface of contact as possible. The projection may also have a parallelepiped, elliptic or also oval cross section. Preferably, the recess will then also be of a corresponding design so as to obtain as large a surface of contact as possible.

Since, preferably, two, in particular three, actuation element pairs are provided, it is preferred that the coupling elements are connected together. In a preferred embodiment this can be achieved by arranging the projections of the first coupling elements such that rotating the coupling elements as one about their common pivot axis causes them to engage into the bifurcated recesses. The bifurcated recesses are correspondingly arranged on a circular line so that the projections can be rotated into the recesses. It is also possible that the bifurcated recesses in the second coupling elements are open to the same direction so that corresponding projections of the first coupling elements can be pushed into all bifurcated recesses at the same time by lateral displacement.

Preferably, the pivot axis of the intermediate element extends substantially perpendicular to the direction of movement of at least one, in particular both actuation elements. Here, the actuation elements are preferably oriented such that the longitudinal axes of the actuation elements are parallel to each other, in particular coaxial with each other.

In a preferred development of the disclosure, the intermediate element comprises an at least segment-shaped disc element, in particular a disc element in the form of a full circle. An outer circumference of the disc element is preferably provided with a groove in which an in particular cable-like connecting element is arranged. Pivoting the intermediate element, in particular by displacing the pivot arm in a tangential direction, thus causes the disc element to rotate or pivot. Thereby, the connecting element is wound up or unwound, depending on the pivoting direction and the arrangement of the cable-like connecting element. For example, winding the connecting element up through a rather small angle causes the transmission of an axial pulling force to the second actuation means. Thus, the connecting element is respectively connected with a second actuation element or passes directly into the second actuation element. For a transmission of axial forces in both directions, it is possible to connect the at least segment-shaped disc element with two connecting elements provided at the outer circumference thereof, the connecting elements preferably being arranged in a groove. Here, the two connecting elements are wound on the disc element in different directions or enclose the disc element in different directions. It is sufficient for the connecting element to enclose the disc element over a certain angle, e.g. 90°. By rotating the disc element correspondingly, one of the two connecting elements is released and the respective other connecting element is pulled.

In another preferred embodiment the pivotable intermediate element comprises a connecting arm that is preferably rigidly connected with the intermediate element. Preferably, the connecting arm is arranged under an angle other than 0 degrees with respect to the pivot arm. Thus, in a preferred embodiment, a linear movement of the second actuation element is translated into a pivoting of the pivot arm. This will cause a corresponding pivoting of the connecting arm. The connecting arm may be connected directly with the second actuation element or it may be connected with the same through further intermediate elements. By providing different arm lengths and/or further intermediate elements, the movement of the first actuation element can be increased or reduced. Preferably, the connecting arm and the second actuation element are connected through elastic connecting elements, in particular in the form of cables. In a preferred embodiment, these are passed over one or a plurality of guide rollers.

According to another embodiment of a surgical manipulation instrument, in which the first and second actuation elements are moved in the axial direction, the connection is realized substantially by screwing a coupling element. Here, in a preferred embodiment, the fastening element pairs are designed such that one of the two fastening elements has a male thread and the other has a projection with a female thread. To avoid having to screw the individual fastening elements separately, a further preferred embodiment provides a ring that surrounds the fastening elements in the region of the coupling. A part of the fastening elements, preferably those with the internal toothing, is rotatably supported in the actuation element so that no turning of the actuation elements is necessary. Further, an elastic component is provided between the actuation elements, which compensates for manufacturing tolerances and allows a simultaneous screwing of all fastening elements. The ring has an inner toothing engaging toothings on the outer circumference of the fastening elements. Thus, rotating this ring causes the rotation of the individual actuation elements about their longitudinal axis. Thereby the actuation elements pairs are screwed together. If so desired, the ring may be driven by another ring, at least one gear being arranged between the two rings in a manner similar to a planet gear. Accordingly, the outer ring comprises an internal toothing, while the inner ring and the intermediate rings have an external toothing. Thereby, a transmission of the rotation and the force and thus a faster or easier opening and closing of the screw connection can be realized. This allows for a much faster coupling and decoupling of the actuation element pairs.

The following is a detailed description of the disclosure with reference to preferred embodiments and to the accompanying drawings.

DETAILED DESCRIPTION OF THE PREFERRED EMBODIMENT

A surgical manipulation instrument according to the present disclosure, which is especially suited for use in minimally invasive surgery, comprises an extra-corporeal drive device 10. The same may, in particular, comprise one or a plurality of electric motors and transmissions whereby actuation elements 12 (FIG. 2) are displaced in the axial direction (arrows 14).

In the embodiment illustrated, the first actuation elements 12 are in the form of rods. However, they may also be cables via which only pulling forces are transmitted.

Figure 1:
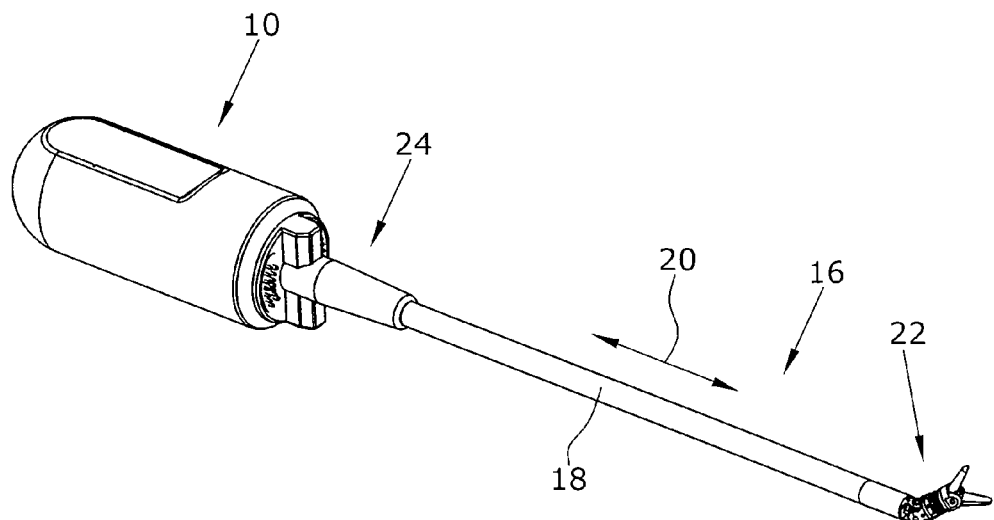
FIG. 1 is a schematic perspective view of a surgical manipulation instrument.

Further, the surgical manipulation instrument comprises a manipulator part 16 (FIG. 1). Within a tubular shaft 18, rod-shaped second actuation elements are arranged. These are adapted to be displaced in the longitudinal direction 20. The second actuation elements are connected with an end effector 22. Displacing the second actuation elements thus causes a manipulation of the end effector. Again, the second actuation elements may be rod-shaped actuation elements, but also actuation cables.

A coupling device 24 is provided for the connection of the first actuation elements 12 and the second actuation elements arranged in the tubular shaft.

Figure 2:
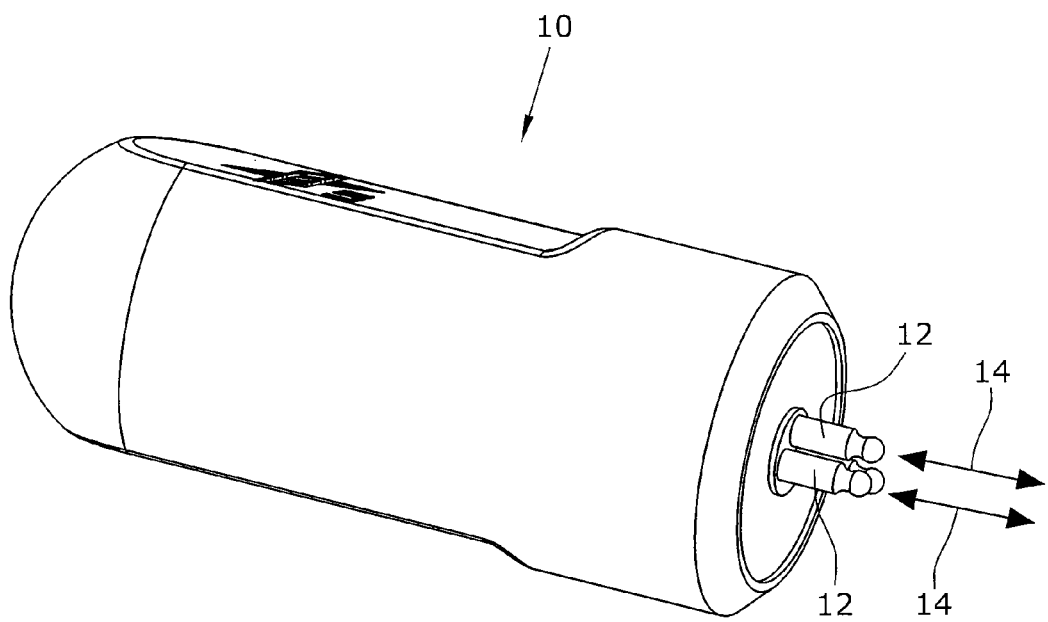
FIG. 2 is a schematic perspective side elevational view of the drive device.
Figure 3:
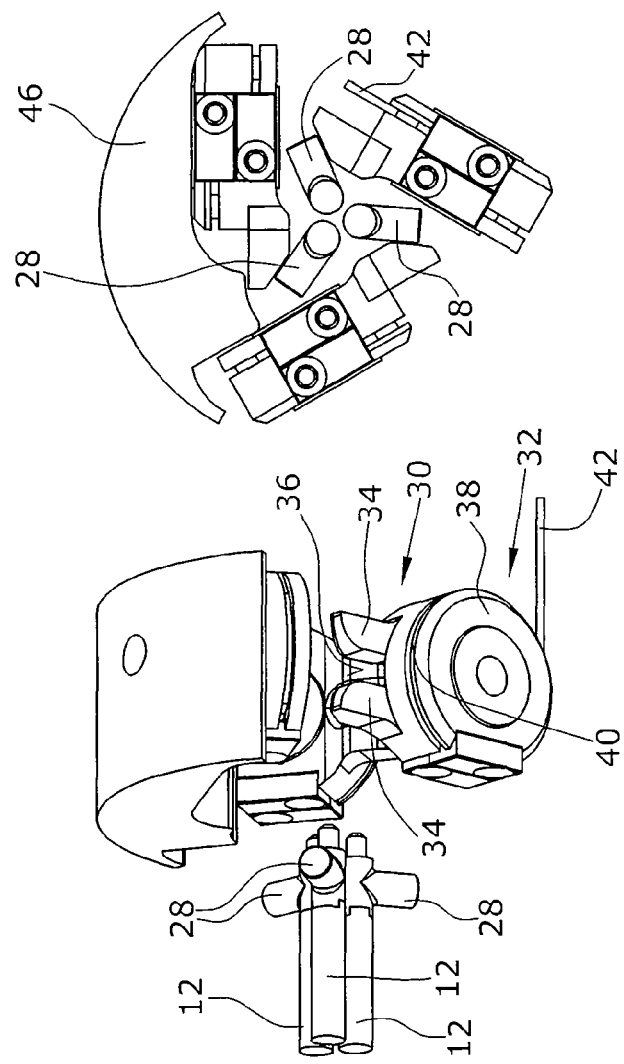
FIG. 3 are schematic illustrations of the first preferred embodiment of the disclosure, in which the actuation devices are not yet coupled with each other by means of the coupling device, FIG. 4 are schematic illustrations of the first preferred embodiment of the disclosure, in which the actuation devices are coupled with each other by means of the coupling device, FIG. 5 are schematic illustrations of a second preferred embodiment of the disclosure, in which the actuation devices are not yet coupled with each other by means of the coupling device, FIG. 6 are schematic illustrations of the second preferred embodiment of the disclosure, in which the actuation devices are coupled with each other by means of the coupling device.
Figure 3:
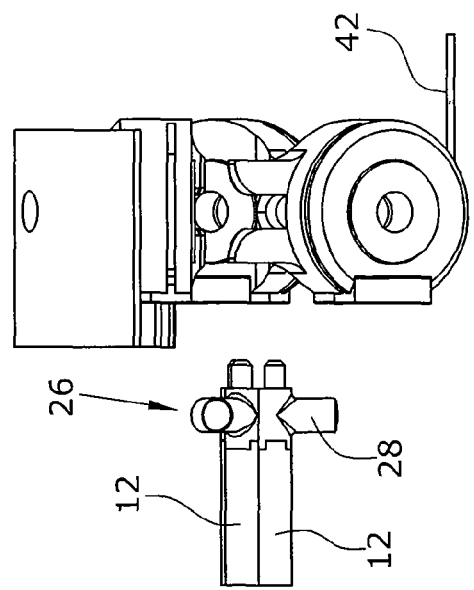

In a first preferred embodiment (FIGS. 3 and 4) the first actuation elements 12 indicated in FIG. 2 are formed as three rods extending in parallel with each other. First coupling elements 26 are provided at the ends of the rods. The coupling elements 26 each have a pin-shaped projection 28. In the embodiment illustrated, the pin-shaped projection 28 is cylindrical and projects outward under an angle of 90 degrees with respect to the longitudinal axis of the first actuation element 12. As obvious in top plan view (FIG. 3, right hand side), the three cylindrical projections 28 are distributed uniformly and thus take on an angle of 120 degrees to each other.

In the embodiment illustrated, second coupling elements 30 have a pivot arm 32. The pivot arm 32 comprises two arm parts 34 extending in parallel with each other so that a bifurcated recess 36 is formed. As described hereinafter, the bifurcated recess 36 receives the pin-shaped projection 28 of the first coupling elements 26.

The pivot arm 32 is rigidly connected with a disc-shaped element 38 of the intermediate element 32.

In the embodiment illustrated, the disc element 38 has a groove 40 in which a cable 42 is arranged. For reasons of clarity, the latter is illustrated only at one of the discs. When the disc element 38 is rotated in a corresponding sense, the cable 42 is pulled. The cable 42 corresponds to the second actuation device or is at least connected with the same.

In order to close the coupling device, all the three first actuation elements 12 are rotated together clockwise, seen in top plan view (FIG. 3, right hand side), so that the projections 28 of the individual coupling elements 26 engage the corresponding bifurcated recesses.

Figure 4:
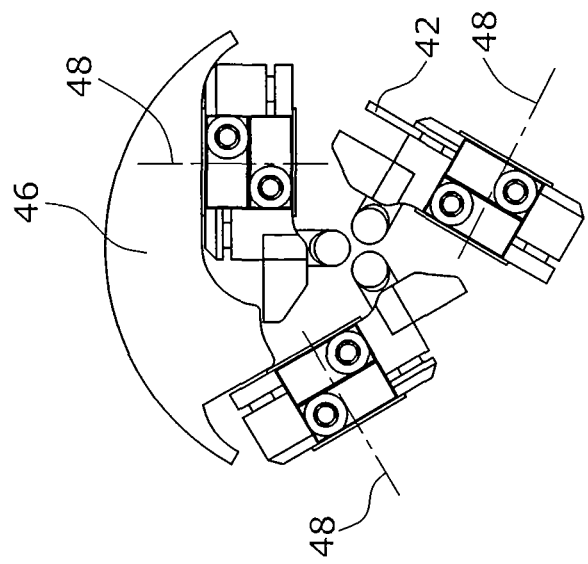
Figure 4:
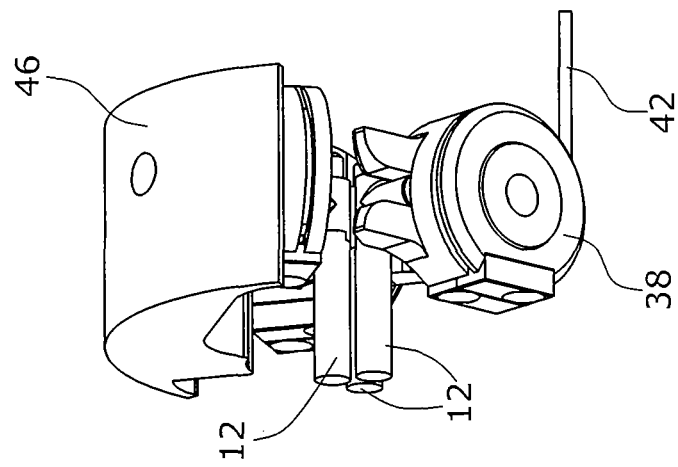
Figure 4:
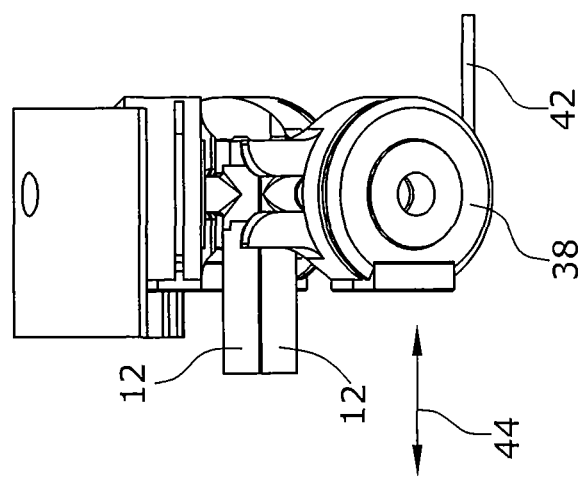

After the coupling of the coupling elements 26, 30, the first actuation elements 12 are adapted to transmit forces onto the second actuation devices 42 by displacement of the former in the direction of an arrow 44 (FIG. 4). Since, in the embodiment illustrated, the second actuation device 42 is a cable, only pulling forces can be transmitted. If, for example, the first actuation element 12 is shifted to the right in FIG. 4, the disc element 48 is rotated clockwise and thereby the only second actuation device 42 illustrated in FIG. 4 is pulled.

The three pivotable intermediate elements 32 of the embodiment illustrated are held in a manner pivotable about pivot axes 48 in a housing 46 illustrated only in part.

In another preferred embodiment of the disclosure (FIGS. 5 and 6) identical and similar components are identified by the same reference numerals.

The first actuation elements 12 are again rod-shaped and have projections 28 that have a different spatial arrangement due to the arrangement of the second coupling elements 30. The bifurcated recesses 36 of the coupling elements 30, numbering three in this embodiment, are arranged one behind the other in the embodiment illustrated in FIG. 5. Accordingly, the lower first actuation element 12 in FIG. 5 has a projection 28 that protrudes from the plane of the drawing. Behind this actuation element 12, a further first actuation element 12 is arranged, whose projection 28 is directed in the opposite direction. The third actuation element 12, which is the top element in FIG. 5, has a projection 28 extending in both directions, which, however, as a shorter length. This projection 28 engages into the central bifurcated opening 36 in FIG. 6.

In the coupled stat, a displacement of the first actuation elements 12 in the longitudinal direction 14 causes the pivot arm 32 to pivot about a pivot axis 50. In the embodiment illustrated, the pivot axes 50 of all intermediate elements 32 are coaxial.

Figure 5:
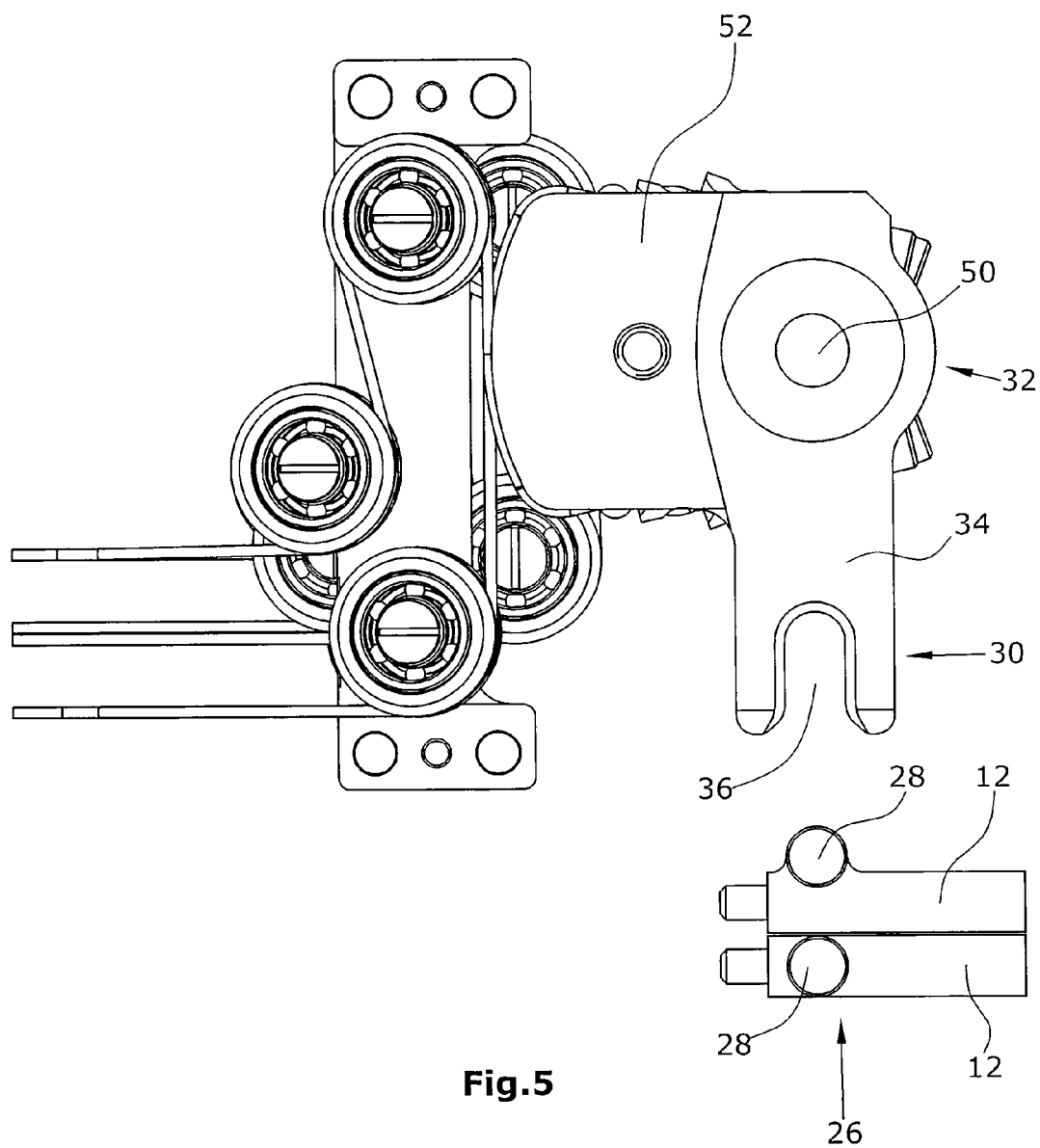
Figure 6:
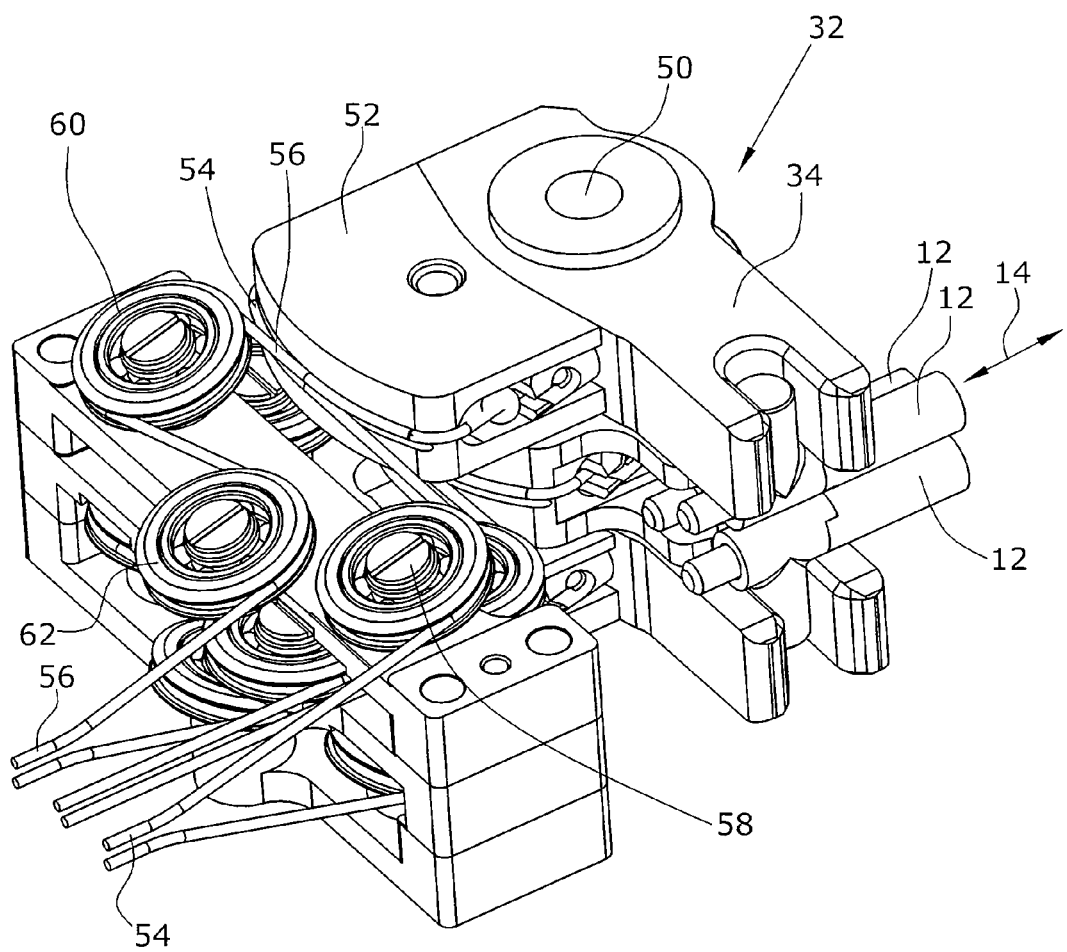

In the embodiment illustrated in FIGS. 5 and 6, the intermediate element 32 is rigidly connected with a respective connecting arm 52. In the embodiment illustrated, the connecting arm 52 of the intermediate elements 32 is at a right angle with respect to the pivot arm 32. The connecting arm 52 is connected with two cables. This is particularly visible for the upper connecting arm 52 in FIG. 6 that is connected with the two cables 54, 56. The two cables 54, 56 are connected to the connecting arm 52 on different sides. Thereby, depending on the sense of rotation of the intermediate element 32, the one or the other cable 54 or 56 is pulled. When the intermediate element 32 in FIG. 6 is pivoted clockwise, the cable 54 is pulled. The latter is passed over a guide roller 58 and is connected with a second actuation element or passes into the second actuation element. When the intermediate element 32 is pivoted counterclockwise (FIG. 6), the cable 56 is pulled. The latter is guided over two guide rollers 60, 62 and then extends in parallel with the cable 54. Depending on the direction of displacement of the first actuation element 12 in the axial direction, the cable 54 or 56 is pulled. In this embodiment, both directions of movement of the first actuation elements can be used even if cables are provided.

In the embodiment illustrated the two other intermediate elements are each also connected with two cables that are also guided over guide rollers. As such, six cables are provided via which pulling forces can be transmitted directly or indirectly to elements of the end effector 22 (FIG. 1) with interposition of second actuation elements.

Figure 7:
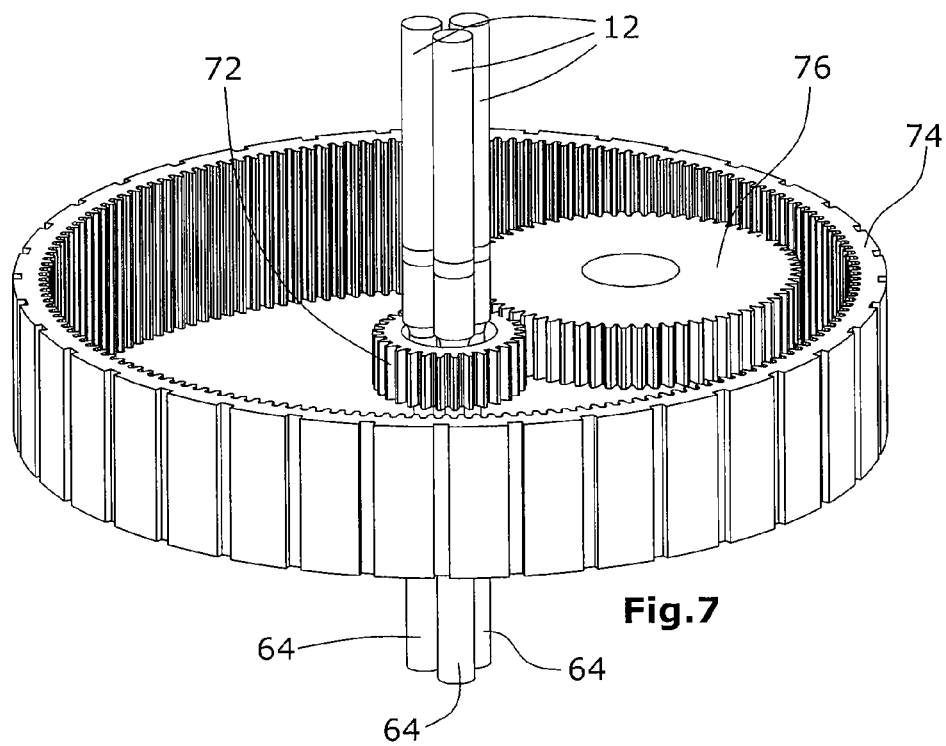
FIG. 7 is a schematic perspective view of a further coupling device for surgical manipulation instruments.
Figure 8:
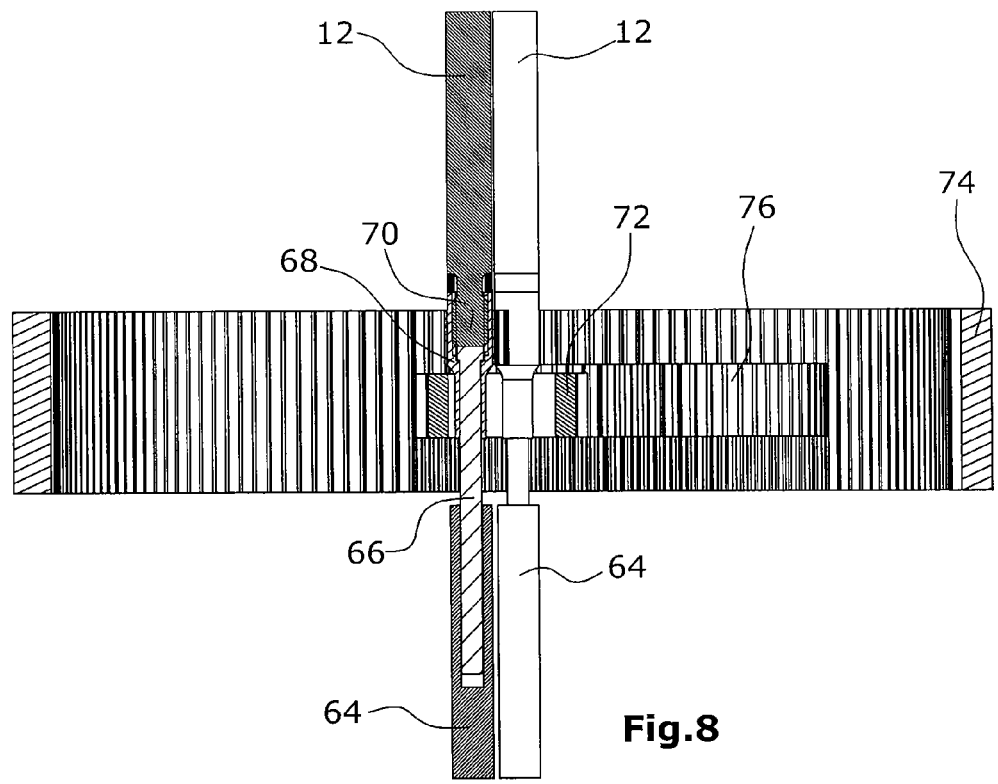
FIG. 8 is a schematic cross sectional view of the coupling device illustrated in FIG. 7.

In another embodiment of a coupling device for a surgical manipulation instrument, actuation element pairs are again provided, wherein the first actuation elements 12 are also rod-shaped. In the embodiment illustrated, the second actuation elements 64 are rod-shaped as well. Corresponding to the above described embodiment, the first actuation elements 12 are connected with the drive device 10 illustrated in FIGS. 1 and 2 and the second actuation elements 64 are connected with the end effector 22. The embodiment illustrated in FIGS. 7 and 8 is an independent disclosure.

In this embodiment, the connection of the actuation element pairs 12-64 is effected by screwing. To this end, the second actuation elements 64 comprises a pin-shaped projection 66 fixedly connected with the second actuation element. The pin-shaped projection 66 is connected with a connecting sleeve 68 having an female thread and adapted to be rotated. The first actuation elements 12 comprise a pin 70 with a male thread at their end directed towards the second actuation element 64. By rotating the connecting sleeves 68 about their longitudinal axis, it is possible to screw, i.e. couple the actuation element pairs 12-64 together without rotating the same.

In order to connect the element pairs 12-64, numbering three in the embodiment illustrated, simultaneously, an inner ring 72 similar to a sun wheel is provided which, in the embodiment illustrated, surrounds the connecting sleeves 68, which have an external toothing, and, in the coupled position, meshes with the teeth of the connecting sleeves. The sun wheel 72 has a female thread cooperating with a thread provided on the outside of the sleeves 68. Thus, by rotating the inner ring 72, the actuation elements 12, 64 are screwed together. In order to allow as fast an opening and closing of the screw connection as possible, an outer ring 74 is provided in the manner of a hand wheel surrounding the sun wheel 72. At least one, preferably three transmission gears 76 are provided as planet wheels between the two rings 72, 74, which mesh with a toothing provided on the inner side of the hand wheel 74 and with a toothing provided on the outer side of the sun wheel 72. In order to compensate for manufacturing tolerances, an elastic compensation element is provided between the actuation element 12 and the connecting sleeve 68, against which compensation element the connecting sleeves 68 are tightened by rotating the sun wheel 72.

The invention claimed is:

1. A surgical manipulation instrument for minimally invasive surgery, comprising:
    an extra-corporeal drive device with a plurality of axially displaceable first actuation elements,
    a partly intra-corporeal manipulator part with a plurality of axially displaceable second actuation elements for the actuation of an end effector, and
    a coupling device for the detachable coupling of actuation element pairs, the coupling device comprises a first coupling element connected with the first actuation element and a second coupling element connected with the second actuation element,
    wherein a pivotable intermediate element is provided between the second coupling element and the second actuation element, by which intermediate element the axial movement of the first actuation element is translated into a pivot movement which is translated by the intermediate element into an axial movement of the second actuation element,
    wherein the second coupling elements comprise a pivot arm that has a bifurcated recess into which engages a projection of the first coupling element, the bifurcated recess is open in the direction of the coupling of said actuation element pairs, the projection extends at an angle of 90 degrees to the direction of the coupling and is offset from an end of the first coupling element, and
    wherein the bifurcated recess is slot shaped so that surface contact between the projection and the recess is as large as possible.

2. The surgical manipulation instrument of claim 1, wherein the pivot arm is rigidly connected with the intermediate element.

3. The surgical manipulation instrument of claim 1, wherein the pivot axis of the intermediate element is substantially perpendicular to the respective direction of movement of the associated first actuation element.

4. The surgical manipulation instrument of claim 1, wherein the intermediate element comprises an at least segment-shaped disc element which has its outer circumference provided with an elastic connecting element connected with the second actuation element.

5. The surgical manipulation instrument of claim 1, wherein the intermediate element comprises a connecting arm which is connected with the pivot arm in a rigid manner.

6. The surgical manipulation instrument of claim 5, wherein the connecting arm is connected with the second actuation element through an elastic connecting element.

7. The surgical manipulation instrument of claim 6, wherein the connecting element is guided over at least one guide roller which forms a part of the intermediate element.

8. The surgical manipulation instrument of claim 5, wherein the connecting arm is connected with two elastic connecting elements so that pulling forces are transmitted via the one or the other connecting element, depending on the pivoting direction.

9. The surgical manipulation instrument of claim 1, wherein the bifurcated recess has a rounded end portion that matches a round outer shape of the projection.

10. A surgical manipulation instrument for minimally invasive surgery, comprising:
    an extra-corporeal drive device with three axially displaceable first actuation elements, each of the first actuation elements having a projection extending at an angle of 90 degrees to a direction of a detachable coupling and at an angle of 120 degrees to each other, a partly intra-corporeal manipulator part with three axially displaceable second actuation elements for the actuation of an end effector, and a coupling device for the detachable coupling of actuation element pairs, the coupling device comprises a first coupling element connected with the first actuation element and a second coupling element connected with the second actuation element, wherein a pivotable intermediate element is provided between the second coupling element and the second actuation element, by the intermediate element the axial movement of the first actuation element is translated into a pivot movement which is translated by the intermediate element into an axial movement of the second actuation element, and wherein the second coupling elements comprise a pivot arm that has a bifurcated recess into which engages the projection of the first coupling element, the bifurcated recess is open in the direction of the detachable coupling of said actuation element pairs.

11. The surgical manipulation instrument of claim 10, wherein the pivot arm is rigidly connected with the intermediate element.

12. The surgical manipulation instrument of claim 10, wherein the pivot axis of the intermediate element is substantially perpendicular to the respective direction of movement of the associated first actuation element.

13. The surgical manipulation instrument of claim 10, wherein the intermediate element comprises an at least segment-shaped disc element which has its outer circumference provided with an elastic connecting element connected with the second actuation element.

14. The surgical manipulation instrument of claim 10, wherein the intermediate element comprises a connecting arm which is connected with the pivot arm in a rigid manner.

15. The surgical manipulation instrument of claim 14, wherein the connecting arm is connected with the second actuation element through an elastic-connecting element.

16. The surgical manipulation instrument of claim 15, wherein the connecting element is guided over at least one guide roller which forms a part of the intermediate element.

17. The surgical manipulation instrument of claim 14, wherein the connecting arm is connected with two elastic connecting elements so that pulling forces are transmitted via the one or the other connecting element, depending on the pivoting direction.

18. The surgical manipulation instrument of claim 10, wherein the bifurcated recess has a rounded end portion that matches a round outer shape of the projection.

* * * * *